(12) United States Patent
Brannan

(10) Patent No.: US 8,968,288 B2
(45) Date of Patent: Mar. 3, 2015

(54) ABLATION DEVICES WITH DUAL OPERATING FREQUENCIES, SYSTEMS INCLUDING SAME, AND METHODS OF ADJUSTING ABLATION VOLUME USING SAME

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 605 days.

(21) Appl. No.: 12/709,014

(22) Filed: Feb. 19, 2010

(65) Prior Publication Data
US 2011/0208177 A1 Aug. 25, 2011

(51) Int. Cl.
*A61B 18/18* (2006.01)
*A61B 18/00* (2006.01)

(52) U.S. Cl.
CPC ... *A61B 18/1815* (2013.01); *A61B 2018/00023* (2013.01); *A61B 2018/1876* (2013.01)
USPC ............................................. 606/33; 606/34

(58) Field of Classification Search
USPC ......... 606/32–34, 41; 607/101, 102, 154–156
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| 5,300,068 A | 4/1994 | Rosar et al. | |
| 5,301,687 A * | 4/1994 | Wong et al. | 607/116 |
| 5,871,525 A * | 2/1999 | Edwards et al. | 607/104 |
| 5,957,969 A * | 9/1999 | Warner et al. | 607/156 |
| 6,016,452 A | 1/2000 | Kasevich | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,398,781 B1 | 6/2002 | Goble et al. | |
| 6,582,427 B1 | 6/2003 | Goble et al. | |
| D496,997 S | 10/2004 | Dycus et al. | |

(Continued)

FOREIGN PATENT DOCUMENTS

DE 390937 3/1924
DE 1099658 2/1961

(Continued)

OTHER PUBLICATIONS

International Search Report EP11001182 dated Jun. 30, 2011.

(Continued)

*Primary Examiner* — Michael Peffley
*Assistant Examiner* — Khadijeh Vahdat

(57) ABSTRACT

An ablation device includes a feedline including an inner conductor having a distal end, an outer conductor coaxially disposed around the inner conductor, and a dielectric material disposed therebetween, an elongated electrically-conductive member longitudinally disposed at the distal end of the inner conductor and having a proximal end, a first balun structure disposed over a first portion of the outer conductor and positioned so that a distal end of the first balun structure is located at a first distance from the proximal end of the electrically-conductive member and a second balun structure disposed over a second portion of the outer conductor and positioned so that a distal end of the second balun structure is located at a second distance from the proximal end of the electrically-conductive member.

18 Claims, 9 Drawing Sheets

(56) References Cited

U.S. PATENT DOCUMENTS

| | | |
|---|---|---|
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,311,703 B2 | 12/2007 | Turovskiy et al. |
| D564,662 S | 3/2008 | Moses et al. |
| 2002/0022836 A1 | 2/2002 | Goble et al. |
| 2003/0153908 A1 | 8/2003 | Goble et al. |
| 2005/0015081 A1* | 1/2005 | Turovskiy et al. ............ 606/33 |
| 2005/0085881 A1* | 4/2005 | Prakash et al. ............. 607/101 |
| 2006/0155270 A1* | 7/2006 | Hancock et al. ............. 606/33 |
| 2008/0033497 A1* | 2/2008 | Bulkes et al. ................. 607/9 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 034 748 | 9/2000 |
| EP | 1 055 400 | 11/2000 |
| EP | 1 159 926 | 5/2001 |
| EP | 2008604 | 12/2008 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 2004047659 | 6/2004 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.

(56) References Cited

OTHER PUBLICATIONS

U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical lmpedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.

(56) References Cited

OTHER PUBLICATIONS

Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.

(56) References Cited

OTHER PUBLICATIONS

European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 12/350,292, filed Jan. 8, 2009.

* cited by examiner

ABLATION DEVICES WITH DUAL
OPERATING FREQUENCIES, SYSTEMS
INCLUDING SAME, AND METHODS OF
ADJUSTING ABLATION VOLUME USING
SAME

BACKGROUND

1. Technical Field

The present disclosure relates to electrosurgical devices suitable for use in tissue ablation applications and, more particularly, to ablation devices with dual operating frequencies, systems including the same, and methods of adjusting ablation volume using the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

In treatment methods utilizing electromagnetic radiation, such as hyperthermia therapy, the transference or dispersion of heat generally may occur by mechanisms of radiation, conduction, and convection. "Thermal radiation" and "radiative heat transfer" are two terms used to describe the transfer of energy in the form of electromagnetic waves (e.g., as predicted by electromagnetic wave theory) or photons (e.g., as predicted by quantum mechanics). In the context of heat transfer, the term "conduction" generally refers to the transfer of energy from more energetic to less energetic particles of substances due to interactions between the particles. The term "convection" generally refers to the energy transfer between a solid surface and an adjacent moving fluid. Convection heat transfer may be a combination of diffusion or molecular motion within the fluid and the bulk or macroscopic motion of the fluid.

The extent of tissue heating may depend on several factors including the rate at which energy is absorbed by, or dissipated in, the tissue under treatment. The electromagnetic-energy absorption rate in biological tissue may be quantified by the specific absorption rate (SAR), a measure of the energy per unit mass absorbed by tissue and is usually expressed in units of watts per kilogram (W/kg). One method to determine the SAR is to measure the rate of temperature rise in tissue as a function of the specific heat capacity of the tissue. This method requires knowledge of the specific heat of the tissue. A second method is to determine the SAR by measuring the electric field strength in tissue. This method requires knowledge of the conductivity and density values of the tissue.

The relationship between radiation and SAR may be expressed as $$SAR = \frac{1}{2}\frac{\sigma}{\rho}|E|^2, \qquad (1)$$

where $\sigma$ is the tissue electrical conductivity in units of Siemens per meter (S/m), $\rho$ is the tissue density in units of kilograms per cubic meter (kg/m$^3$), and $|E|$ is the magnitude of the local electric field in units of volts per meter (V/m).

The relationship between the initial temperature rise $\Delta T$ (° C.) in tissue and the specific absorption rate may be expressed as $$\Delta T = \frac{1}{c}SAR\Delta t, \qquad (2)$$

where c is the specific heat of the tissue (in units of Joules/kg-° C.), and $\Delta t$ is the time period of exposure in seconds (sec). Substituting equation (1) into equation (2) yields a relation between the induced temperature rise in tissue and the applied electric field as $$\Delta T = \frac{1}{2}\frac{\sigma}{\rho c}|E|^2\Delta t. \qquad (3)$$

As can be seen from the above equations, modifying the local electric-field amplitude directly affects the local energy absorption and induced temperature rise in tissue. In treatment methods such as hyperthermia therapy, it would be desirable to deposit an electric field of sufficient magnitude to heat malignant tissue to temperatures above 41° C. while limiting the SAR magnitude in nearby healthy tissue to be less than that within the tumor to keep the healthy cells below the temperature causing cell death.

Fluid-cooled or dielectrically-buffered microwave devices may be used in ablation procedures. During operation of a microwave ablation device, if proper cooling is not maintained, e.g., flow of coolant or buffering fluid is interrupted, the microwave ablation device may exhibit rapid failures due to the heat generated from the increased reflected power. Cooling the ablation probe may enhance the overall heating pattern of the antenna and prevent damage to the antenna.

During certain procedures, it can be difficult to assess the extent to which the microwave energy will radiate into the surrounding tissue, making it difficult to determine the area or volume of surrounding tissue that will be ablated. Tissue ablation devices capable of influencing the SAR and the ablation volume may enable more precise ablation treatments, which may lead to shorter patient recovery times, fewer complications from undesired tissue damage, and improved patient outcomes.

SUMMARY

The present disclosure relates to an ablation device including a feedline that includes an inner conductor having a distal end, an outer conductor coaxially disposed around the inner conductor, and a dielectric material disposed therebetween. The ablation device also includes an elongated electrically-conductive member longitudinally disposed at the distal end of the inner conductor and having a proximal end, a first balun structure disposed over a first portion of the outer conductor and positioned so that a distal end of the first balun structure is located at a first distance from the proximal end of the electrically-conductive member, and a second balun structure disposed over a second portion of the outer conductor and positioned so that a distal end of the second balun structure is located at a second distance from the proximal end of the electrically-conductive member.

The present disclosure relates to a system including a generator assembly and an ablation device operably associated with the generator assembly. The ablation device includes a feedline having an inner conductor, an outer conductor coaxially disposed around the inner conductor, and a dielectric material disposed therebetween. The ablation device also includes a first balun structure operably associated with a first operating frequency, wherein the first balun structure is electrically coupled to the outer conductor, and a second balun structure operably associated with the second operating frequency, wherein the second balun structure is electrically coupled to the outer conductor.

The present disclosure also relates to a method of adjusting ablation volume including the initial step of positioning in tissue an ablation device capable of operating at a first operating frequency and a second operating frequency. The ablation device includes an antenna assembly configured with a first balun operably associated with the first operating frequency and a second balun operably associated with the second operating frequency. The method also includes the steps of transmitting energy from an energy source through the antenna assembly to tissue at the first operating frequency, and transmitting energy from the energy source through the antenna assembly to tissue at the second operating frequency.

BRIEF DESCRIPTION OF THE DRAWINGS

Objects and features of the presently disclosed ablation devices with dual operating frequencies, systems including the same, and methods of adjusting ablation volume using the same will become apparent to those of ordinary skill in the art when descriptions of various embodiments thereof are read with reference to the accompanying drawings, of which.

DETAILED DESCRIPTION

Figure 1:
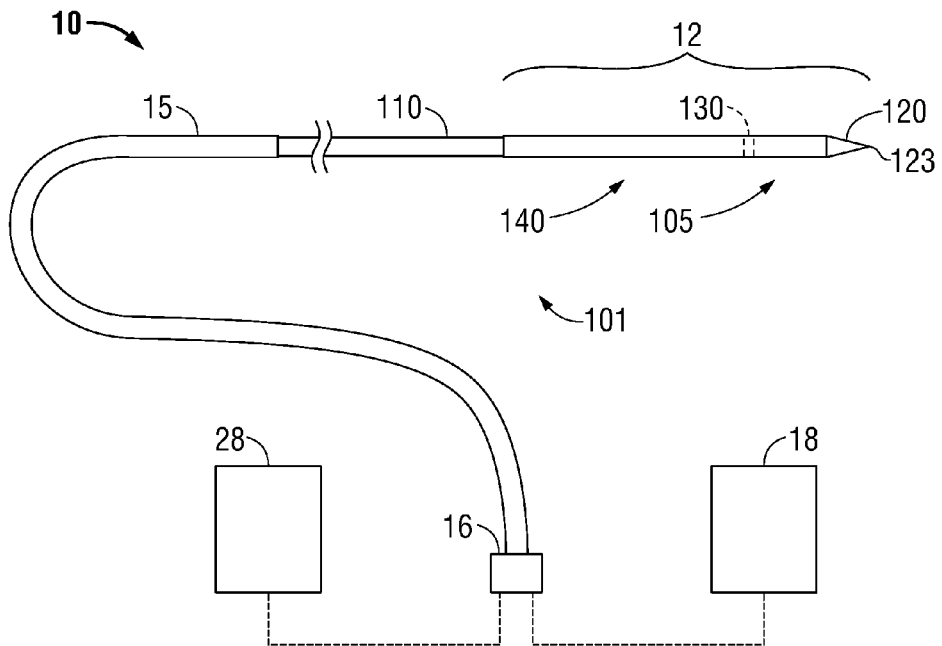
FIG. 1 is a schematic diagram of an ablation system in accordance with an embodiment of the present disclosure.

Hereinafter, embodiments of the presently disclosed ablation devices with dual operating frequencies, systems including the same, and methods of adjusting ablation volume using the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the ablation device, or component thereof, closer to the user and the term "distal" refers to that portion of the ablation device, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "NB" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "energy applicator array" generally refers to one or more energy applicators. As it is used in this description, "transmission line" generally refers to any transmission medium that can be used for the propagation of signals from one point to another. As it is used in this description, "fluid" generally refers to a liquid, a gas or both.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide ablation devices with dual operating frequencies for treating tissue and methods of directing electromagnetic radiation to tissue. The presently disclosed ablation device according to various embodiments is configured with a first balun structure operably associated with a first operating frequency and a second balun structure operably associated with a second operating frequency. Although the following description describes ablation devices with dual operating frequencies, the teachings of the present disclosure may also apply to ablation devices with a plurality of operating frequencies. Embodiments may be implemented using electromagnetic radiation at microwave frequencies or at other frequencies. In some embodiments, the presently disclosed ablation device is capable of operating at a first operating frequency of about 915 MHz and a second operating frequency of about 2.45 GHz. In some embodiments, the second operating frequency may be about 5.8 GHz. In some embodiments, the presently disclosed ablation device is capable of operating at a first operating frequency of about 915 MHz, a second operating frequency of about 2.45 GHz and a third operating frequency of about 5.8 GHz. An electrosurgical system including the presently disclosed ablation device in fluid communication with a coolant supply system according to various embodiments is designed and configured to operate at frequencies between about 500 MHz and about 10 GHz.

Various embodiments of the presently disclosed ablation device with dual operating frequencies are suitable for microwave ablation and for use to pre-coagulate tissue for microwave ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10, according to an embodiment of the present disclosure that includes an energy applicator or probe 101. An embodiment of an energy applicator, such as the probe 101 of FIG. 1, in accordance with the present disclosure, is shown in more detail in FIG. 2. It will be understood, however, that other probe embodiments may also be used (e.g., 301 and 701 shown in FIGS. 3 and 7, respectively).

Figure 2:
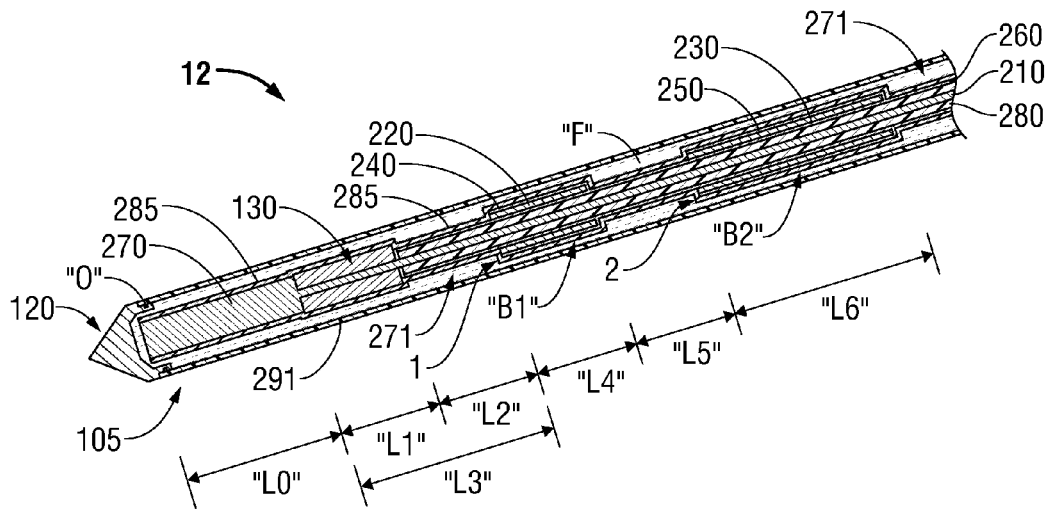
FIG. 2 is a partial, longitudinal cross-sectional view of an embodiment of the energy applicator of the ablation system shown in FIG. 1 in accordance with the present disclosure.

Probe 101 generally includes an antenna assembly 12 having a radiating portion connected by a feedline 110 (or shaft) via a transmission line 15 to a connector 16, which may further operably connect the probe 101 to an electrosurgical power generating source 28, e.g., a microwave or RF electrosurgical generator. As shown in FIG. 2, the probe 101 may include a first balun structure "B1" having a length "L4" and a second balun structure "B2" having a length "L6". In some embodiments, the first balun structure "B1" may be a quarter-wave sleeve balun or a half-wave sleeve balun. In some embodiments, the second balun structure "B2" may be a quarter-wave sleeve balun or a half-wave sleeve balun. The shape, size and relative positions of the first balun structure "B1" and the second balun structure "B2", which are described in more detail later in this disclosure, may be varied from the configuration depicted in FIG. 2.

Feedline 110 may be formed from a suitable flexible, semi-rigid or rigid microwave conductive cable and may connect directly to an electrosurgical power generating source 28. Alternatively, the feedline 110 may electrically connect the antenna assembly 12 via the transmission line 15 and connector 11 to the electrosurgical power generating source 28. Feedline 110 may have a variable length from a proximal end of the antenna assembly 12 to a distal end of transmission line 15 ranging from a length of about one inch to about twelve inches. Feedline 110 may be formed of suitable electrically-conductive materials, e.g., copper, gold, silver or other conductive metals or metal alloys having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof, the stainless steel may be coated with a layer of a conductive material such as copper or gold.

Feedline 110 may include an inner conductor 210, a dielectric material 280 coaxially surrounding the inner conductor 210, and an outer conductor 260 coaxially surrounding the dielectric material 280. Antenna assembly 12 may be formed from a portion of the inner conductor 210 that extends distal to the feedline 110 into the antenna assembly 12. Dielectric material 280 may be formed from any suitable dielectric material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, or metal oxides. Inner conductor 210 and the outer conductor 260 may be formed from any suitable electrically conductive material. In some embodiments, the inner conductor 210 is formed from a first electrically conductive material (e.g., stainless steel) and the outer conductor 260 is formed from a second electrically conductive material (e.g., copper). Feedline 110 may be cooled by fluid, e.g., saline, water or other suitable coolant fluid, to improve power handling, and may include a stainless steel catheter.

The presently disclosed antenna assembly 12 includes an elongated electrically-conductive element 270. In some embodiments, the electrically-conductive element 270 is a solid metal cylinder that is electrically coupled to the inner conductor 210 (e.g., by solder). Electrically-conductive element 270 may be formed of any suitable electrically-conductive material (e.g., metal such as stainless steel, aluminum, titanium, copper, etc.) of any suitable length "L0". The shape and size of the electrically-conductive element 270 may be varied from the configuration depicted in FIG. 2.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant fluid from a coolant source 18 to one or more components of the probe 101.

An end cap or tapered portion 120 located at the distal end of the antenna assembly 12 terminates in a sharp tip 123 to allow for insertion into tissue with minimal resistance. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. A junction member 130 may be disposed between the proximal and distal radiating portions, 140 and 105, respectively. In some embodiments, the distal and proximal radiating portions 105, 140 align at the junction member 130, which is generally made of a dielectric material, e.g., adhesives, and are also supported by the inner conductor that extends at least partially through the distal radiating portion 105. Junction member 130 may have any suitable length "L1", and may be formed from any suitable elastomeric or ceramic dielectric material by any suitable process. In some embodiments, the junction member 130 is formed by over-molding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction member 130 may be formed using any suitable over-molding compound by any suitable process, and may include use of a ceramic substrate.

As shown in FIG. 2, the presently disclosed antenna assembly 12 includes a first balun structure "B1" having a length "L4" and a second balun structure "B2" having a length "L6" disposed proximal to the first balun structure "B1". In some embodiments, the second balun structure "B2" may be spaced apart, by a length "L5", from the first balun structure "B1". In some embodiments, the second balun structure "B2", or portions thereof, may overlap the first balun structure "B1", or portions thereof. In some embodiments, the distal end of the second balun structure "B2" may be disposed substantially adjacent to the proximal end of the first balun structure "B1". In some embodiments, the first balun structure "B1" may be spaced apart, by a length "L3", from the proximal end of the electrically-conductive element 270. In some embodiments, the first balun structure "B1" may be spaced apart, by a length "L2", from the proximal end of the junction member 130.

First balun structure "B1" according to various embodiments includes a first balun insulator 220 disposed about the outer conductor 260, and a first electrically-conductive layer 240 (also referred to herein as a first conductive balun sleeve) disposed about the first balun insulator 220, or portions thereof. First conductive balun sleeve 240 is electrically coupled to the outer conductor 260, e.g., by solder or other suitable electrical connection. Second balun structure "B2" according to various embodiments includes a second balun insulator 230 disposed about the outer conductor 260, and a second electrically-conductive layer 250 (also referred to herein as a second conductive balun sleeve) disposed about the second balun insulator 230, or portions thereof. Second conductive balun sleeve 250 is electrically coupled to the outer conductor 260 using any suitable electrical connection. In some embodiments, the proximal end of the first conductive balun sleeve 240 and/or the proximal end of the second conductive balun sleeve 250 may be adapted to allow for connection, e.g., electrically and mechanically, to the outer conductor 260.

First and second balun insulators 220 and 230, respectively, may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. First and second balun insulators 220, 230 may be grown, deposited or formed by any other suitable technique. In some embodiments, the first and second balun insulators 220, 230 are formed from a material with a dielectric constant in the range of about 1.7 to about 10. First and second electrically-conductive layers 240 and 250, respectively, may be formed of any suitable electrically-conductive material, e.g., metal such as stainless steel, titanium, copper, etc., and may be formed in any suitable manner.

In some embodiments, the antenna assembly 12 may be provided with a coolant chamber (e.g., 271 shown in FIG. 2). Additionally, the junction member 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS", the disclosures of which are incorporated herein by reference in their entireties.

In some embodiments, the antenna assembly 12 may be provided with an outer dielectric layer (e.g., 285 shown in FIG. 2) disposed about the proximal radiating portion 140, the junction 130, and/or the distal radiating portion 105, or portions thereof. The outer dielectric layer may be formed of any suitable material, such as, for example, polymeric or ceramic materials. The outer dielectric layer may be applied by any suitable method, such as, for example, heat shrinking, over-molding, coating, spraying dipping, powder coating, baking and/or film deposition.

As shown in FIG. 2, the antenna assembly 12 includes an outer jacket 291. Outer jacket 291 may have a substantially cylindrical or tubular shape. In some embodiments, the distal end of the outer jacket 291 is adapted to be coupleable to an end cap or tapered portion 120, e.g., by an O-ring "O", or other suitable connection method or device. Outer jacket 291 and the end cap or tapered portion 120 may be formed as a single structure. The shape and size of the outer jacket 291 and the tapered portion 120 may be varied from the configuration depicted in FIG. 2.

Outer jacket 291 may be a fluid-cooled catheter formed of a composite material having low electrical conductivity, e.g., glass-reinforced polymers. According to embodiments of the present disclosure, a coolant chamber 271 is defined between the outer dielectric layer 285 and the outer jacket 291. Coolant chamber 271 may be adapted to circulate coolant fluid "F" around the electrically-conductive element 270. Coolant fluid "F" may be any suitable fluid that can be used for cooling or buffering the probe 101, e.g., deionized water, or other suitable cooling medium. Coolant fluid "F" may have dielectric properties and may provide dielectric impedance buffering for the antenna assembly 12.

During microwave ablation, e.g., using the electrosurgical system 10, the probe 101 is inserted into or placed adjacent to tissue and microwave energy is supplied thereto. Ultrasound or computed tomography (CT) guidance may be used to accurately guide the probe 101 into the area of tissue to be treated. Probe 101 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 101 may depend on the progress of the heat distribution within the tissue area that is to be destroyed and/or the surrounding tissue. Single or multiple probes 101 may provide ablations in short procedure times, e.g., a few minutes, to destroy cancerous cells in the target tissue region. Treatment of certain tumors may involve probe repositioning during the ablation procedure, such as where the tumor is larger than the probe or has a shape that does not correspond with available probe geometry or radiation pattern.

A plurality of probes 101 may be placed in variously-arranged configurations to substantially simultaneously ablate a target tissue region, making faster procedures possible. Multiple probes 101 can be used to synergistically create a large ablation or to ablate separate sites simultaneously. Tissue ablation size and geometry is influenced by a variety of factors, such as the energy applicator design, number of energy applicators used simultaneously, ablation time and wattage, and tissue characteristics.

In operation, microwave energy having a wavelength, lambda (A), is transmitted through the antenna assembly 12, e.g., along the proximal and distal radiating portions 140, 105, and radiated into the surrounding medium, e.g., tissue. The length of the antenna for efficient radiation may be dependent on the effective wavelength $\lambda_{eff}$, which is dependent upon the dielectric properties of the medium being radiated. Antenna assembly 12 through which microwave energy is transmitted at a wavelength λ may have differing effective wavelengths $\lambda_{eff}$ depending upon the surrounding medium, e.g., liver tissue as opposed to breast tissue.

Figure 3:
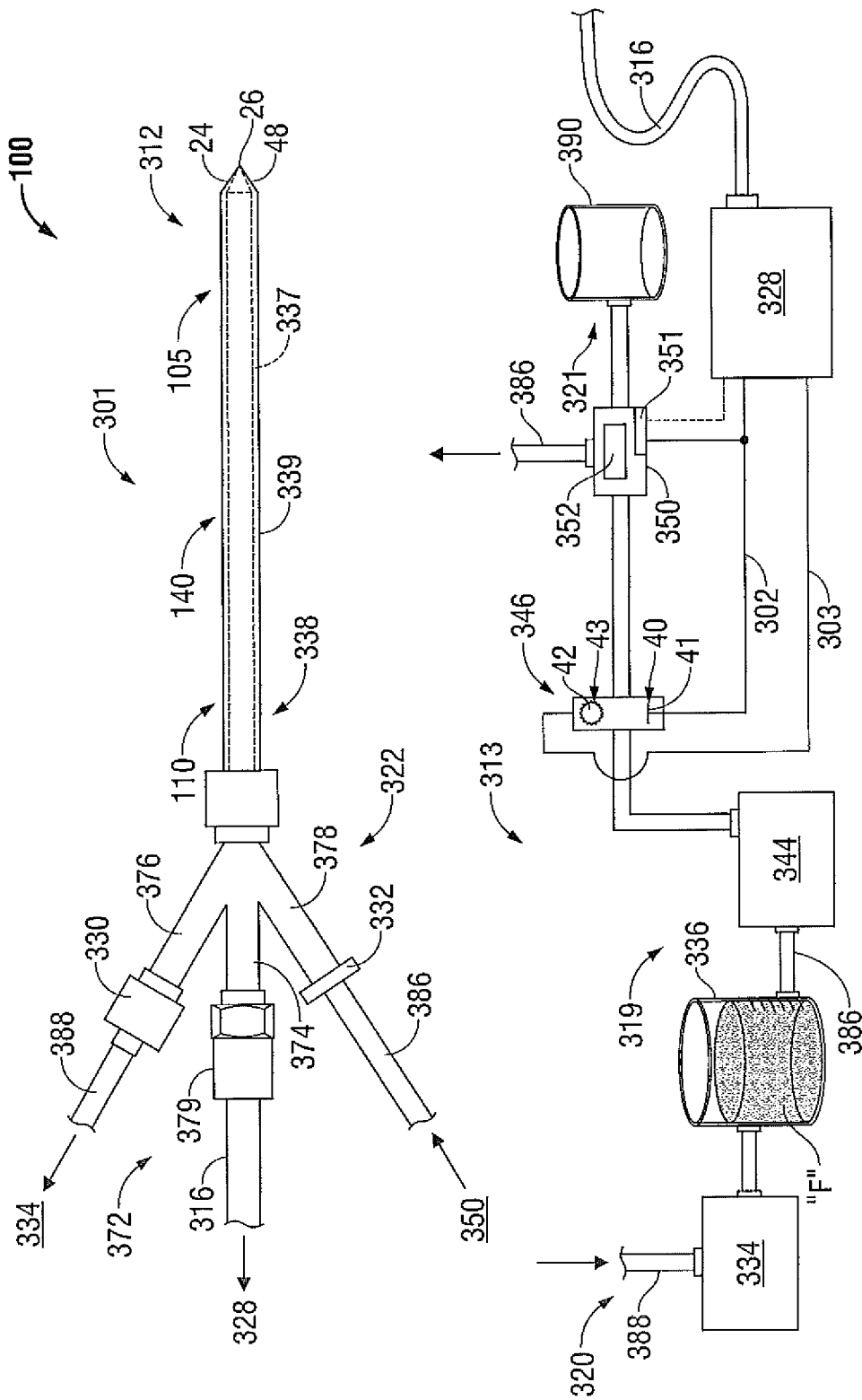
FIG. 3 is a schematic diagram of another embodiment of an ablation system in accordance with the present disclosure.

FIG. 3 shows an electrosurgical system 100 according to an embodiment of the present disclosure that includes an ablation device 301. Ablation device 301 includes an antenna assembly 312 disposed within a sheath 338. Ablation device 301 according to various embodiments includes a tip 48 having a tapered end 24 that terminates, in one embodiment, at a pointed end 26 to allow for insertion into tissue with minimal resistance. In some embodiments, a feedline 110 couples the antenna assembly 312 to a connection hub 322. Connection hub 322, which is described in more detail later in this disclosure, generally includes a cable connector 379 and fluid ports 330 and 332. Electrosurgical system 100 generally includes a coolant supply system 313. Examples of coolant supply system embodiments are disclosed in commonly assigned U.S. patent application Ser. No. 12/566,299 filed on Sep. 24, 2009, entitled "OPTICAL DETECTION OF INTERRUPTED FLUID FLOW TO ABLATION PROBE". Antenna assembly 312 is similar to the antenna assembly 12 shown in FIG. 2 and further description thereof is omitted in the interests of brevity.

Sheath 338 generally includes a substantially tubular member 339 defining a lumen into which the antenna assembly 312, or portions thereof, may be positioned. In some embodiments, the sheath 338 is disposed over and encloses the feedline 110, the proximal radiating portion 140 and the distal radiating portion 105. Sheath 338 according to various embodiments may be a water-cooled catheter, which may be configured to be coupleable to the tip 48. In accordance with the embodiment shown in FIG. 3, a coolant chamber 337 is defined between the tubular member 339 and the outer surfaces of the feedline 110, the proximal radiating portion 140 and the distal radiating portion 105.

Coolant chamber 337 is adapted to circulate coolant fluid "F" therethrough, and may include baffles, multiple lumens, flow restricting devices, or other structures that may redirect, concentrate, or disperse flow depending on their shape. Examples of coolant chamber embodiments are disclosed in commonly assigned U.S. patent application Ser. No. 12/350, 292 filed on Jan. 8, 2009, entitled "CHOKED DIELECTRIC LOADED TIP DIPOLE MICROWAVE ANTENNA". The size and shape of the sheath 338 and the coolant chamber 337 extending therethrough may be varied from the configuration depicted in FIG. 3.

Electrosurgical system 100 in accordance with an embodiment of the present disclosure includes a power generating source 328, a coolant supply system 313 adapted to provide coolant fluid "F" via a connection hub 322 to the antenna assembly 312, and a sensor unit 346 capable of detecting a gas bubble in the coolant supply system 313 and electrically coupled via transmission lines 302 and 303 to the power generating source 328. Electrosurgical system 100 may further include a flow-diverter apparatus 350 operably associated with the sensor unit 346 and disposed in fluid communication between the sensor unit 346 and the connection hub 322. In some embodiments, when the sensor unit 346 detects an air or other gas bubble in the coolant supply system 313, the sensor unit 346 transmits an electrical signal via transmission line 302 to the power generating source 328 and the flow-diverter apparatus 350.

Coolant supply system 313 generally includes a coolant source 336, a first coolant path 319 leading from the coolant source 336 to the connection hub 322, and a second coolant path 320 leading from the connection hub 322 to the coolant source 336. In some embodiments, the first coolant path 319 includes a first fluid movement device 344 configured to move coolant fluid "F" through the first coolant path 319, and the second coolant path 320 includes a second fluid movement device 334 configured to move coolant fluid "F" through the second coolant path 320.

Coolant source 336 may be any suitable housing containing a reservoir of coolant fluid "F", and may maintain coolant fluid "F" at a predetermined temperature. For example, the coolant source 336 may include a cooling unit (not shown) that cools the returning coolant fluid "F" from the antenna assembly 312. Coolant fluid "F" may be any suitable fluid that can be used for cooling or buffering the probe 301, e.g., deionized water, or other suitable cooling medium. Coolant fluid "F" may have dielectric properties and may provide dielectric impedance buffering for the antenna assembly 312. Coolant fluid "F" may be a conductive fluid, such as a saline solution, which may be delivered to the target tissue, e.g., to influence impedance and allow increased power to be delivered to the target tissue. A coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

Connection hub 322 may have a variety of suitable shapes, e.g., cylindrical, rectangular, etc. In some embodiments, the connection hub 322 includes a cable connector 379, an outlet fluid port 330 and an inlet fluid port 332. Connection hub 322 may include a three-branch luer type connector 372 having a middle branch 374 used to house the cable connector 379 and two outer branches 376 and 378 to house the outlet and inlet fluid ports 330 and 332, respectively. Connection hub 322 may be adapted to be connected in fluid communication with the sheath 338. In some embodiments, the sheath 338 is coupled to the connection hub 322 and the tip 48, thereby defining a chamber 337 around the feedline 110, the proximal radiating portion 140 and the distal radiating portion 105. Connector 379 may be adapted to be connected to a cable 316 to operably connect the probe 301 to a power generating source 328.

In some embodiments, the first coolant path 319 includes a coolant supply line 386 leading from the coolant source 336 to the inlet fluid port 332. First fluid movement device 344 may be disposed in fluid communication between the inlet fluid port 332 and the coolant source 336. In some embodiments, the second coolant path 320 includes a coolant return line 388 leading from the outlet fluid port 330 to the coolant source 336. Second fluid movement device 334 may be disposed in fluid communication between the outlet fluid port 330 and the coolant source 336. The positions of the first fluid movement device 344 and the second fluid movement device 334, e.g., in relation to the coolant source 336, may be varied from the configuration depicted in FIG. 3.

In some embodiments, a controller 351 associated with the flow-diverter apparatus 350 may actuate a fluid flow diverter 352 to divert coolant fluid "F" flow to a third coolant fluid path 321. Fluid flow diverter 352 may be any suitable device for selectively diverting the coolant fluid "F" flow. Third coolant fluid path 321 may lead from the flow-diverter apparatus 350 to a container 390. Controller 351 may include any type of computing device, computational circuit, or any type of processor or processing circuit capable of executing a series of instructions that are stored in a memory (not shown) of the controller 351.

In some embodiments, the flow-diverter apparatus 350 includes a valve (not shown) that includes a valve body and an electromechanical actuator operatively coupled to the valve body. Controller 351 may control fluid flow diverter 352 by activating the actuator, e.g., according to a predetermined valve control sequence. In some embodiments, a valve control sequence may involve moving the valve from a first position, in which coolant fluid "F" flows towards the connection hub 322, to a second position, in which the coolant fluid "F" having an air or other gas bubble entrained therein flows into the container 390, and returning to the first position, e.g., after a predetermined time interval, thereby re-establishing coolant fluid "F" flow towards the connection hub 322.

Figure 4:
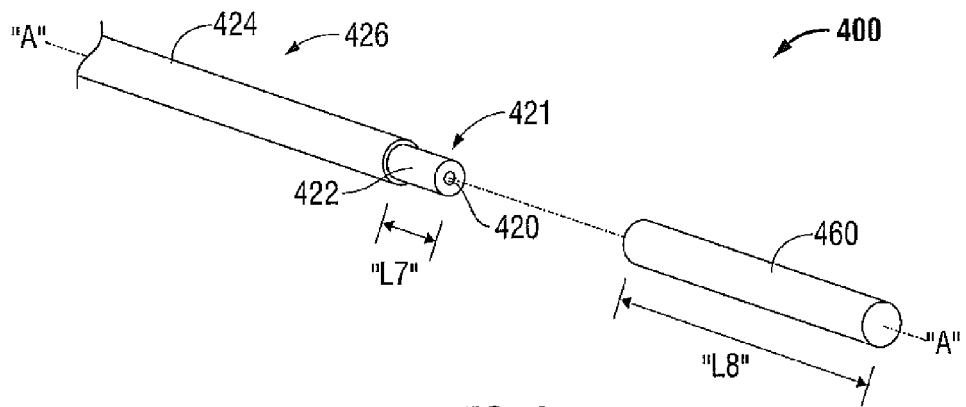
FIG. 4 is a perspective view with parts disassembled of a portion of an energy applicator according to an embodiment of the present disclosure.
Figure 6A:
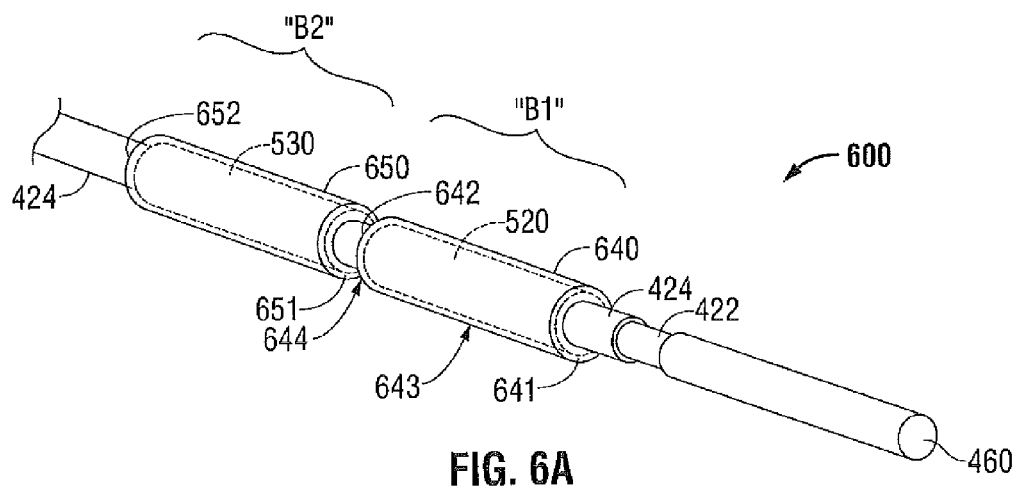
FIG. 6A is a perspective view of the energy applicator of FIG. 5 shown with first and second electrically-conductive layers disposed about the first and second dielectric layers, respectively, according to an embodiment of the present disclosure.
Figure 6B:
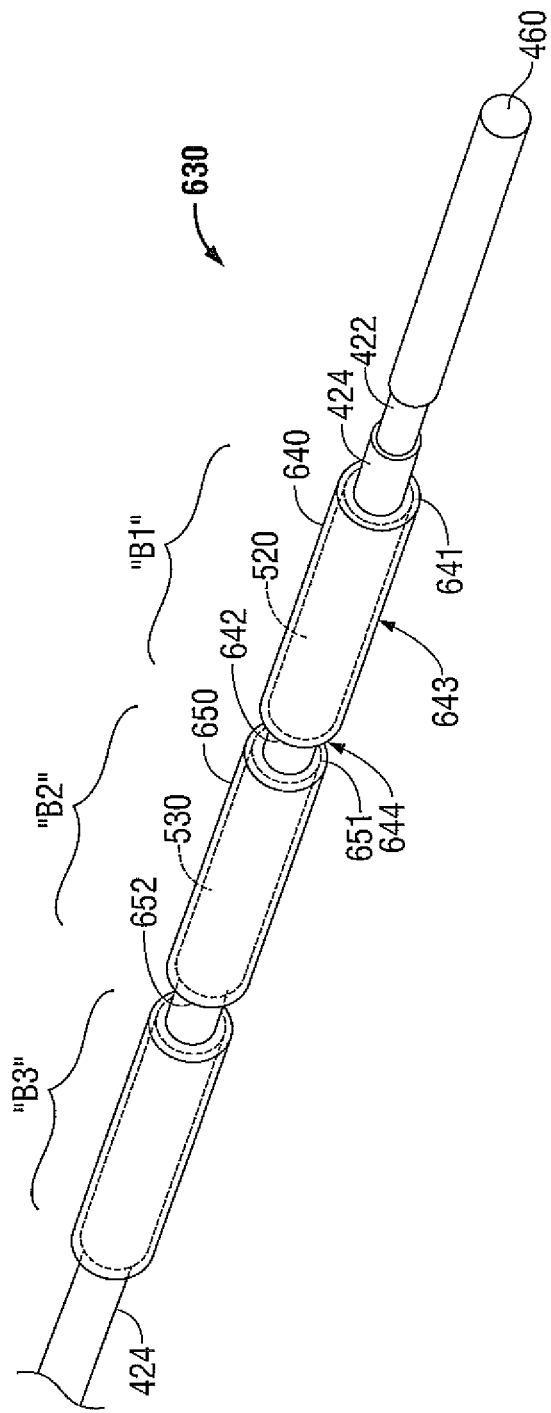
FIG. 6B is a perspective view of the energy applicator of FIG. 6A shown with a third balun structure according to an embodiment of the present disclosure.
Figure 7:
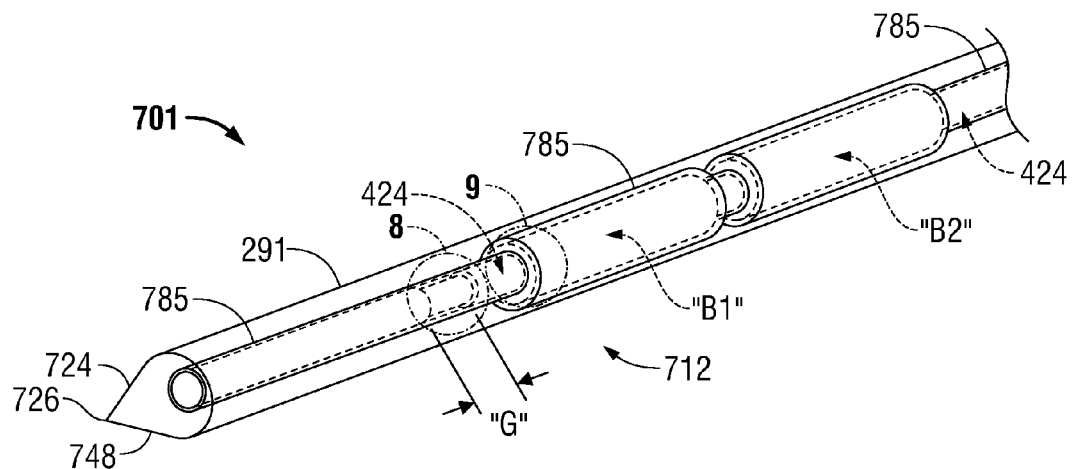
FIG. 7 is a partial, perspective view of an embodiment of an ablation device including the portion of the energy applicator of FIG. 6A shown surrounded by an outer dielectric layer and disposed within an outer jacket in accordance with the present disclosure.

FIGS. 4 through 7 show a sequentially-illustrated, assembly of components forming an ablation device or probe, shown generally as 701 in FIG. 7, in accordance with the present disclosure. In FIG. 4, a coaxial feedline 426 is shown with the outer conductor 424 trimmed back, such that a portion 421 of the dielectric material 422 and the inner conductor 420, having a length "L7", extends beyond the outer conductor 424. According to an embodiment of the present disclosure, an energy applicator segment shown generally as 400 in FIG. 4 includes an electrically-conductive element 460 that extends along the longitudinal axis "A" of the inner conductor 420. Electrically-conductive element 460 may be positioned in a distal portion of the ablation device 701. In some embodiments, the electrically-conductive element 460 is a solid metal cylinder disposed at the distal end of the portion 421 electrically coupled to the inner conductor 420 (e.g., by solder). Electrically-conductive element 460 may be formed of any suitable electrically-conductive material (e.g., metal such as stainless steel, aluminum, titanium, copper, etc.) of any suitable length "L8". The shape and size of the electrically-conductive element 460 may be varied from the configuration depicted in FIG. 4.

Figure 5:
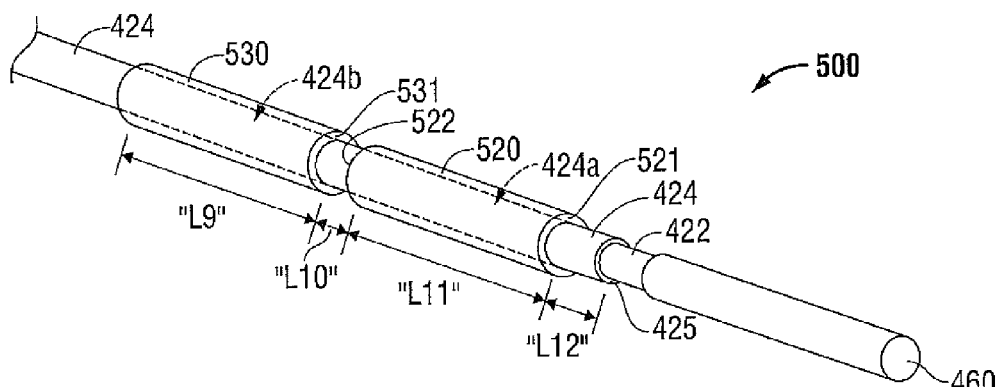
FIG. 5 is a perspective, assembled view of the energy applicator of FIG. 4 shown with first and second dielectric layers disposed about first and second portions of the outer conductor, respectively, according to an embodiment of the present disclosure.

FIG. 5 shows an energy applicator segment 500 according to an embodiment of the present disclosure that is similar to the energy applicator segment 400 of FIG. 4, except for a first dielectric layer 520 (also referred to herein as a balun insulator) disposed coaxially about a first portion 424a of the outer conductor 424 and a second dielectric layer 530 disposed coaxially about a second portion 424b of the outer conductor 424. First balun insulator 520 may have a suitable length "L11" in a range from about 0.1 inches to about 3.0 inches. First balun insulator 520 may be spaced apart from and disposed proximal to the distal end 425 of the outer conductor 424. In some embodiments, the distal end 521 of the first balun insulator 520 is spaced apart, by a length "L12", e.g., about 0.1 inches, from the distal end 425 of the outer conductor 424. Second balun insulator 530 may have a suitable length "L9" in a range from about 0.1 inches to about 3.0 inches. In some embodiments, the distal end 531 of the second balun insulator 530 may be disposed substantially adjacent to the proximal end 522 of the first balun insulator 520. As shown in FIG. 5, the distal end 531 of the second balun insulator 530 may be spaced apart, by a length "L10", from and disposed proximal to the proximal end 522 of the first balun insulator 520.

First and second balun insulators 520, 530 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. First and second dielectric layers 520, 530 may be grown, deposited or formed by any other suitable technique. In some embodiments, the first dielectric layer 520 is formed from a material with a dielectric constant in the range of about 1.7 to about 10. The shape, size and relative positions of the first balun insulator 520 and the second balun insulator 540 may be varied from the configuration depicted in FIG. 5. In some embodiments, the first balun insulator 520 may extend distally beyond the distal end of a conductive balun sleeve (e.g., 640 shown in FIG. 6A) to direct current into a balancing/unbalancing (balun) structure (e.g., "B1" shown in FIG. 6A).

FIG. 6A shows an energy applicator segment 600 according to an embodiment of the present disclosure that is similar to the energy applicator segment 500 of FIG. 5 except for a first electrically-conductive layer 640 (also referred to herein as a conductive balun sleeve) disposed coaxially about the first balun insulator 520 and a second electrically-conductive layer 650 disposed coaxially about the second balun insulator 530. As shown in FIG. 6A the first electrically-conductive layer 640 includes a proximal end 642 and a distal end 641, and the second electrically-conductive layer 650 includes a proximal end 652 and a distal end 651.

First electrically-conductive layer 640 may have any suitable length. In some embodiments, the first electrically-conductive layer 640 has a length of about 0.1 inches to about 3.0 inches. First electrically-conductive layer 640 may be formed as a single structure and electrically coupled to the outer conductor 424, e.g., by solder or other suitable electrical connection. In some embodiments, the first electrically-conductive layer 640 includes a first portion 643 disposed coaxially about a proximal portion of the first balun insulator 520, and a second portion 644 disposed proximally to the first portion 643 electrically coupled to the outer conductor 424. First and second portions 643, 644 may be formed of any suitable electrically-conductive material, e.g., metal such as stainless steel, titanium, copper, etc., and may be formed in any suitable manner. First and second portions 643, 644 may be formed separately from each other. First and second portions 643, 644 may form a single, unitary structure. Second electrically-conductive layer 650 is similar to the first electrically-conductive layer 640 of FIG. 6A and further description thereof is omitted in the interests of brevity. The shape and size of the first electrically-conductive balun sleeve 640 and the second electrically-conductive balun sleeve 650 may be varied from the configuration depicted in FIG. 6A.

FIG. 6B shows an energy applicator segment 630 according to an embodiment of the present disclosure that is similar to the energy applicator segment 600 of FIG. 6A except for a third balun structure "B3". Third balun structure "B3" is similar to the second balun structure "B2" of FIG. 6A and further description thereof is omitted in the interests of brevity. The shape and size of the first balun structure "B1", the second balun structure "B2", and the third balun structure "B3" may be varied from the configurations depicted in FIG. 6B.

FIG. 7 shows an ablation device 701 according to an embodiment of the present invention that includes an antenna assembly 712 disposed within a sheath 291. Antenna assembly 712 is similar to the energy applicator segment 600 shown in FIG. 6A, except for an outer dielectric layer 785. Outer dielectric layer 785 may configured to prevent direct contact between the coolant fluid "F" and the antenna assembly 712. Outer dielectric layer 785, in an embodiment, is a sleeve of fluorinated ethylene propylene (FEP) shrink wrap, and may be applied to the entire length of the antenna assembly 712. In some embodiments, the ablation device 701 includes a tip 748 having a tapered end 724 that terminates at a pointed end 726 to allow for insertion into tissue with minimal resistance.

Figure 8:
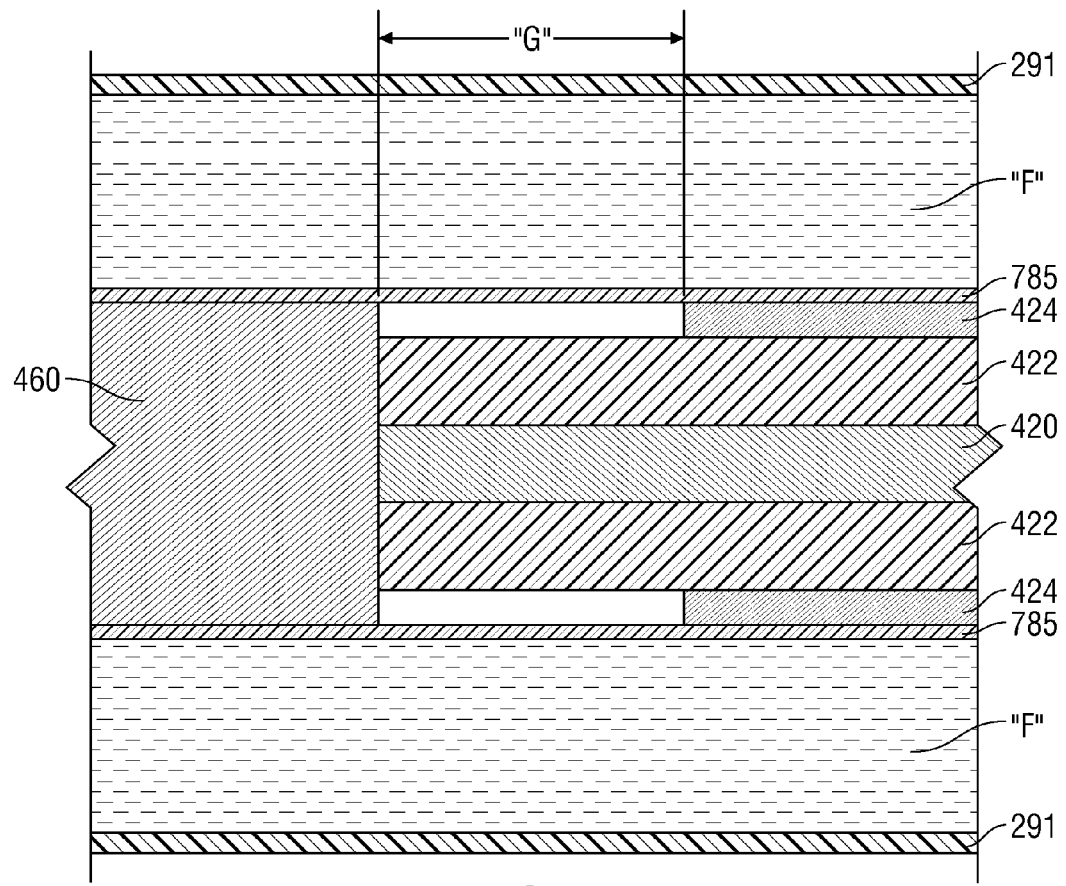
FIG. 8 is an enlarged, cross-sectional view of the indicated area of detail of FIG. 7 according to an embodiment of the present disclosure.
Figure 9:
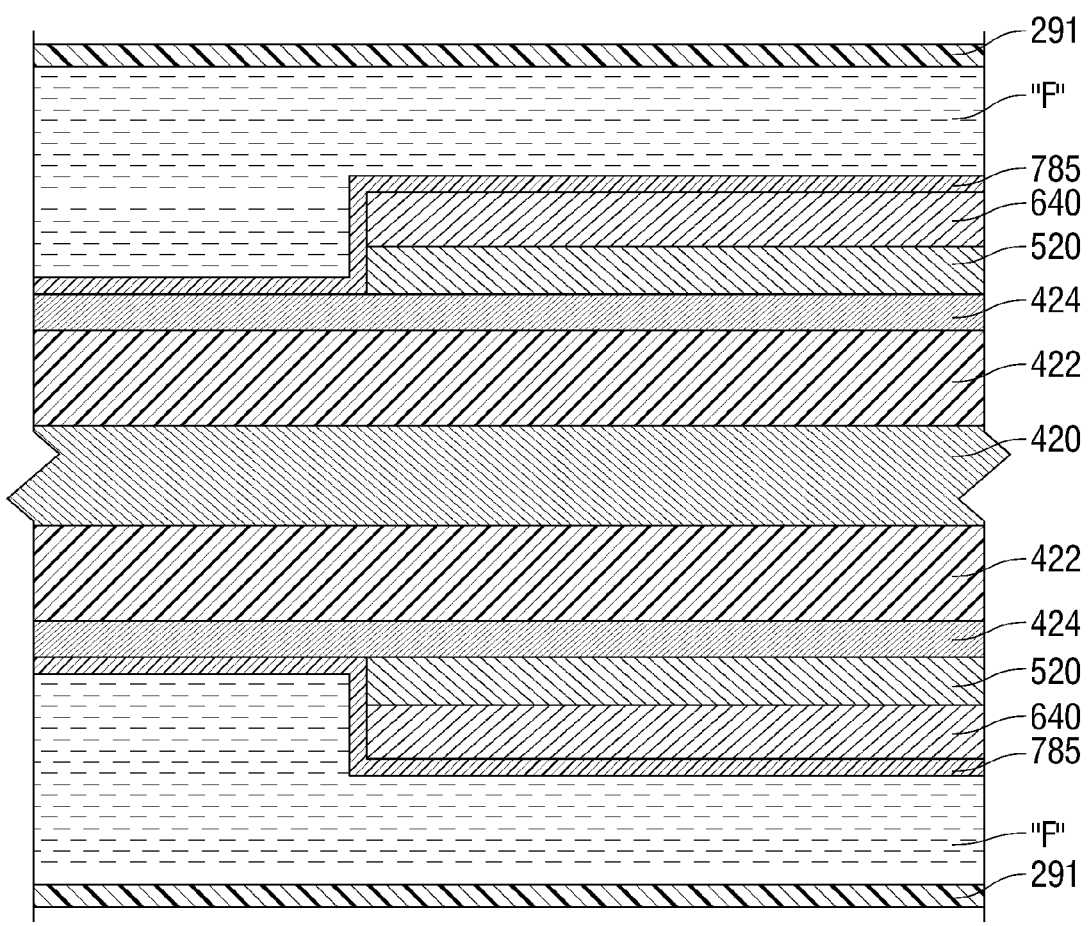
FIG. 9 is an enlarged, cross-sectional view of the indicated area of detail of FIG. 7 according to an embodiment of the present disclosure.

As shown in FIGS. 7 and 8, a dipole feed gap "G" is defined between the proximal end of the electrically-conductive element 460 and the distal end (e.g., 425 shown in FIG. 5) of the outer conductor 424. In some embodiments, the feed gap "G" may be from about 1 mm to about 3 mm. As shown in FIGS. 7 and 9, the outer dielectric layer 785 may be configured to cover the outer conductor 424 and the first balun insulator 520 and the first conductive balun sleeve 640 of first balun structure "B1".

Figure 10:
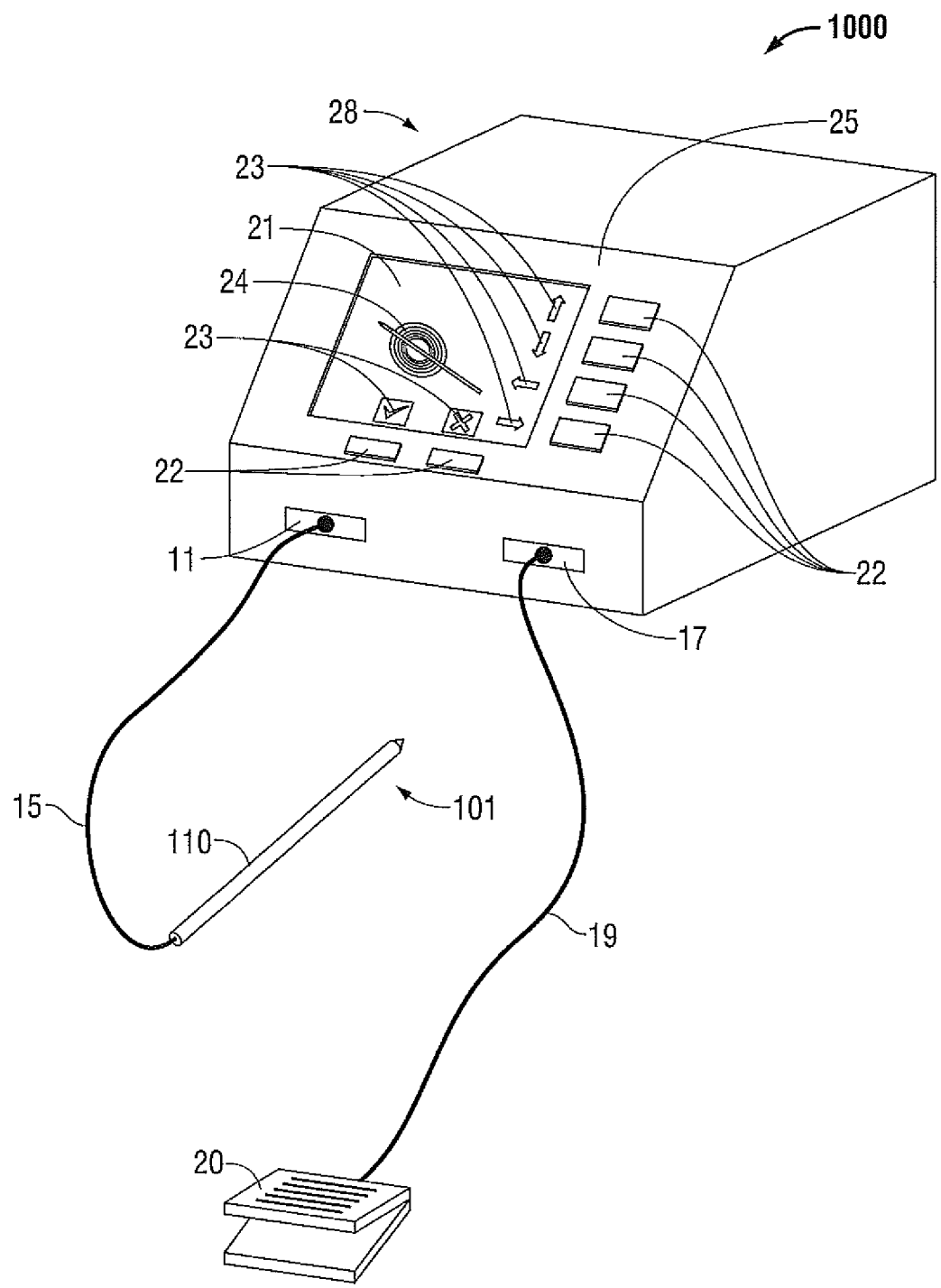
FIG. 10 shows a diagram of a microwave ablation system that includes a user interface for displaying and controlling ablation patterns in accordance with the present disclosure.

FIG. 10 schematically illustrates an electrosurgical system 1000 according to an embodiment of the present disclosure including the ablation device or probe 101. It will be understood, however, that other probe embodiments (e.g., 301 and 701 shown in FIGS. 3 and 7, respectively) may also be used. Electrosurgical system 1000 includes an actuator 20 operably coupled by a cable 19 via connector 17 to an embodiment of the generator assembly 28 of the electrosurgical system 10 of FIG. 1. Actuator 20 may be a footswitch, a handswitch, a bite-activated switch, or any other suitable actuator. Cable 19 may include one or more electrical conductors for conveying an actuation signal from the actuator 20 to the generator assembly 28. In an embodiment, the actuator 20 is operably coupled to the generator assembly 28 by a wireless link, such as without limitation, a radiofrequency or infrared link. In use, the clinician may interact with the user interface 25 to preview operational characteristics of the ablation device 101.

Generator assembly 28, according to various embodiments, includes a generator module (e.g., 86 shown in FIG. 11) in operable communication with a processor (e.g., 82 shown in FIG. 11), a user interface 25, and an actuator 20. Ablation device 101 is operably coupled to an energy output of the generator module, which may be configured as a source of RF and/or microwave energy. Actuator 20 is operably coupled to the processor via the user interface 25. In embodiments, actuator 20 may be operably coupled to the processor and/or to the generator module by a cable connection or a wireless connection.

User interface 25 may include a display 21, such as without limitation a flat panel graphic LCD (liquid crystal display), adapted to visually display at least one user interface element 23, 24. In an embodiment, display 21 includes touchscreen capability (not shown), e.g., the ability to receive input from an object in physical contact with the display, such as without limitation, a stylus or a user's fingertip. A user interface element 23, 24 may have a corresponding active region, such that, by touching the screen within the active region associated with the user interface element, an input associated with the user interface element 23, 24 is received by the user interface 25.

User interface 25 may additionally, or alternatively, include one or more controls 22 that may include without limitation a switch (e.g., pushbutton switch, toggle switch, slide switch) and/or a continuous actuator (e.g., rotary or linear potentiometer, rotary or linear encoder). In an embodiment, a control 22 has a dedicated function, e.g., display contrast, power on/off, and the like. Control 22 may also have a function that may vary in accordance with an operational mode of the electrosurgical system 1000. A user interface element 23 may be positioned substantially adjacently to control 22 to indicate the function thereof. Control 22 may also include an indicator, such as an illuminated indicator, e.g., a single- or variably-colored LED indicator.

Figure 11:
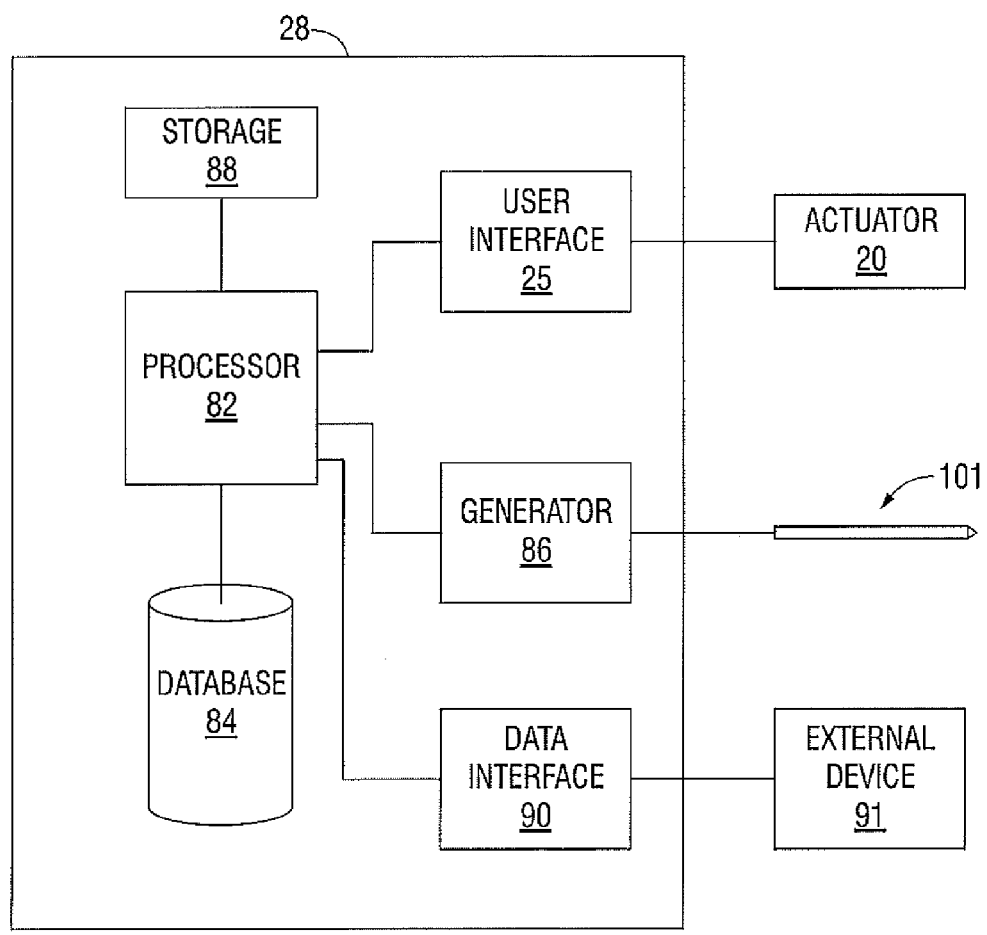
FIG. 11 is a block diagram of a microwave ablation system in accordance with the present disclosure.

FIG. 11 is a block diagram showing one embodiment of the electrosurgical system 1000 of FIG. 10. In an embodiment, the generator module 86 is configured to provide energy of about 915 MHz. Generator module 86 may additionally, or alternatively, be configured to provide energy of about 2450 MHz (2.45 GHz) or about 5800 MHz (5.8 GHz). The present disclosure contemplates embodiments wherein the generator module 86 is configured to generate a frequency other than about 915 MHz or about 2450 MHz or about 5800 MHz, and embodiments wherein the generator module 86 is configured to generate variable frequency energy. Generator assembly 28 includes a processor 82 that is operably coupled to the user interface 25. Processor 82 may include any type of computing device, computational circuit, or any type of processor or processing circuit capable of executing a series of instructions that are stored in a memory, e.g., storage device 88 or external device 91.

In some embodiments, a storage device 88 is operably coupled to the processor 82, and may include random-access memory (RAM), read-only memory (ROM), and/or non-volatile memory (NV-RAM, Flash, and disc-based storage.) Storage device 88 may include a set of program instructions executable on the processor 82 for executing a method for displaying and controlling ablation patterns in accordance with the present disclosure. Generator assembly 86 may include a data interface 90 that is configured to provide a communications link to an external device 91. In some embodiments, the data interface 90 may be any of a USB interface, a memory card slot (e.g., SD slot), and/or a network interface (e.g., 100 BaseT Ethernet interface or an 802.11 "Wi-Fi" interface.) External device 91 may be any of a USB device (e.g., a memory stick), a memory card (e.g., an SD card), and/or a network-connected device (e.g., computer or server).

Generator assembly 28 may also include a database 84 that is configured to store and retrieve energy applicator data, e.g., parameters associated with one or energy applicators (e.g., 101 shown in FIG. 11). Parameters stored in the database 84 in connection with an energy applicator, or energy applicator array assembly, may include, but are not limited to, energy applicator (or applicator array assembly) identifier, energy applicator (or applicator array assembly) dimensions, a frequency, an ablation length (e.g., in relation to a radiating section length), an ablation diameter, a gap distance at the feed point (e.g., in relation to an ablation geometry), a temporal coefficient, a shape metric, and/or a frequency metric. In an embodiment, ablation pattern topology may be included in the database 84, e.g., a wireframe model of an applicator array assembly and/or an ablation pattern associated therewith.

Database 84 may also be maintained at least in part by data provided by the external device 91 via the data interface 90. For example without limitation, energy applicator data may be uploaded from an external device 91 to the database 84 via the data interface 90. Energy applicator data may additionally, or alternatively, be manipulated, e.g., added, modified, or deleted, in accordance with data and/or instructions stored on the external device 91. In an embodiment, the set of energy applicator data represented in the database 84 is automatically synchronized with corresponding data contained in the external device 91 in response to the external device 91 being coupled (e.g., physical coupling and/or logical coupling) to the data interface 90.

Processor 82 according to various embodiments is programmed to enable a user, via the user interface 25 and/or the display 21, to view at least one ablation pattern and/or other energy applicator data corresponding to an embodiment of an applicator array assembly. For example, a surgeon may determine that a substantially spherical ablation pattern is necessary. The surgeon may activate a "select ablation shape" mode of operation for generator assembly 28, preview an energy applicator array by reviewing graphically and textually presented data on the display 21, optionally, or alternatively, manipulate a graphic image by, for example, rotating the image, and select an array of energy applicators based upon displayed parameters. The selected energy applicator(s) may then be electrically coupled to the generator assembly 28 for use therewith.

In an embodiment, a surgeon may input via the user interface 25 an applicator array parameter to cause the generator assembly 28 to present one or more electromagnetic energy delivery devices corresponding thereto. For example, a surgeon may require a 3.0 cm×3.0 cm ablation pattern, and provide an input corresponding thereto. In response, the generator assembly 28 may preview a corresponding subset of available electromagnetic energy delivery devices that match or correlate to the inputted parameter.

In an embodiment, a surgeon may input via the user interface 25 a selected power output, and the electrosurgical system 1000 controls the ablation device 101 to automatically adjust the ablation volume by changing the operating frequency of the ablation device 101, e.g., based on the power level and/or level of reflected power. Electrosurgical system 1000 according to various embodiments may include a feedback looping mechanism suitable for use in controlling an embodiment of an ablation device in accordance with the present disclosure. The feedback looping mechanism may include, without limitation, proximity sensors, a voltage divider network, radial sensors, and/or feedback clicks, e.g., based upon the thread ratio of the threads 357a, 358a.

Hereinafter, a method of adjusting ablation volume, in accordance with the present disclosure, is described with reference to FIG. 12. It is to be understood that the steps of the methods provided herein may be performed in combination and in a different order than presented herein without departing from the scope of the disclosure.

Figure 12:
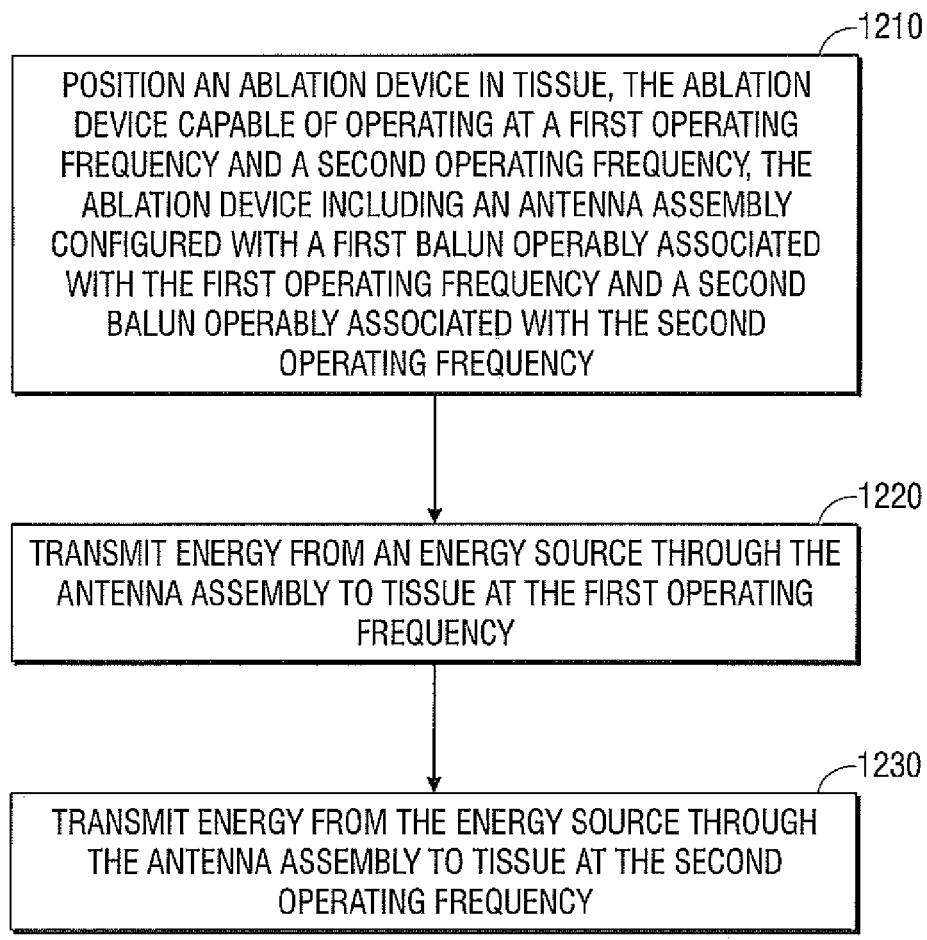
FIG. 12 is a flowchart illustrating a method of directing energy to tissue according to an embodiment of the present disclosure.

FIG. 12 is a flowchart illustrating a method of adjusting ablation volume according to an embodiment of the present disclosure. In step 1210, an ablation device (e.g., 701 shown in FIG. 7) capable of operating at a first operating frequency and a second operating frequency is positioned in tissue. The ablation device may be inserted directly into tissue, inserted through a lumen, e.g., a vein, needle or catheter, placed into the body during surgery by a clinician, or positioned in the body by other suitable methods known in the art. The ablation device includes an antenna assembly (e.g., 712 shown in FIG. 7) configured with a first balun (e.g., "B1" shown in FIG. 7) operably associated with the first operating frequency and a second balun (e.g., "B2" shown in FIG. 7) operably associated with the second operating frequency. The first balun may be a quarter-wave sleeve balun. In some embodiments, the ablation device may also include a third balun (e.g., "B3" shown in FIG. 6B) operably associated with a third operating frequency.

In step 1220, energy is transmitted from an energy source (e.g., 28 shown in FIG. 1) through the antenna assembly (e.g., 712 shown in FIG. 7) to tissue at the first operating frequency. In some embodiments, the first operating frequency may be about 915 MHz.

In step 1230, energy is transmitted from the energy source through the antenna assembly to tissue at the second operating frequency. In some embodiments, the second operating frequency may be about 2.45 GHz. In accordance with an embodiment of the presently disclose method of directing energy to tissue adjusting the ablation field radiating about at least a portion of the ablation device by selectively transmitting energy through the antenna assembly to tissue at the first operating frequency and the second operating frequency.

The above-described ablation devices with dual operating frequencies and methods of adjusting ablation volume according to embodiments of the present disclosure may allow clinicians to avoid ablating or unnecessarily heating tissue structures, such as large vessels, healthy organs or vital membrane barriers, by adjusting the ablation volume.

The above-described electrosurgical systems including the presently disclosed ablation devices may enable a user to view one or more ablation patterns and/or other energy applicator data corresponding to a particular ablation device, which may allow clinicians to predict ablation volume, avoid complications, and/or plan for treatment margins. The above-described electrosurgical systems may be adapted to automatically adjust the operating frequency of the presently disclosed ablation devices with dual operating frequencies, e.g., to adjust the ablation volume.

The above-described ablation devices may be designed to operate at a first operating frequency of about 915 MHz, and a second operating frequency of about 2.45 GHz or about 5.8 GHz, or any other applicable frequencies. In some embodiments, the presently disclosed ablation devices include a first balun structure adapted to allow for operation at a first frequency and a second balun structure adapted to allow for operation at a second frequency, and electrosurgical systems including the same may be operated at a first frequency, e.g., about 915 MHz, wherein the distal radiating section has a first length, e.g., about 4 cm, and a second frequency, e.g., about 2.45 GHz, wherein the distal radiating section is adjusted to have a second length, e.g., about 2 cm. In some embodiments, the second balun structure may be adapted to allow for operation at a second frequency of about 5.8 GHz, wherein the distal radiating section is adjusted to have a length of about 1 cm.

In some embodiments, the presently disclosed ablation devices include a first balun structure adapted to allow for operation at a first frequency (e.g., about 915 MHz), a second balun structure adapted to allow for operation at a second frequency (e.g., about 2.45 GHz) and a third balun structure adapted to allow for operation at a third frequency (e.g., about 5.8 GHz).

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An ablation device, comprising:
a feedline including an inner conductor having a distal end and a first diameter, an outer conductor coaxially disposed around the inner conductor, and a dielectric material disposed therebetween;
an elongated electrically-conductive member longitudinally-disposed at the distal end of the inner conductor and having a proximal end and a second diameter different than the first diameter;
a dielectric layer coaxially disposed around a first portion of the outer conductor;
a first balun disposed over the first portion of the outer conductor and positioned so that a distal end of the first balun is located at a first distance from the proximal end of the elongated electrically-conductive member, the first balun including an electrically-conductive layer coaxially disposed around a proximal portion of the dielectric layer, wherein the dielectric layer extends distally beyond a distal-most end of the inner conductor; and
a second balun disposed over a second portion of the outer conductor and positioned so that a distal end of the second balun is located at a second distance from the proximal end of the elongated electrically-conductive member.

2. The ablation device of claim 1, wherein the first balun is operably associated with a first operating frequency.

3. The ablation device of claim 2, wherein the first balun is a quarter-wave sleeve balun.

4. The ablation device of claim 2, wherein the first operating frequency is about 915 MHz.

5. The ablation device of claim 1, wherein the second balun is operably associated with a second operating frequency.

6. The ablation device of claim 5, wherein the second operating frequency is about 2.45 GHz.

7. The ablation device of claim 5, further comprising a third balun structure, wherein the third balun is operably associated with a third operating frequency.

8. The ablation device of claim 1, wherein a portion of the inner conductor and the dielectric material of the feedline extend beyond the outer conductor at a distal end of the feedline.

9. The ablation device of claim 1, further comprising a sheath including a substantially tubular member defining a lumen therein, wherein the lumen is configured to contain at least a portion of the ablation device therein.

10. The ablation device of claim 9, wherein the lumen is configured to contain the elongated electrically-conductive member and the first and second baluns therein.

11. The ablation device of claim 10, further comprising a coolant chamber defined between the substantially tubular member and the elongated electrically-conductive member and the first and second baluns.

12. The ablation device of claim 11, further comprising an outer dielectric layer disposed over at least a portion of the elongated electrically-conductive member and the first and second baluns.

13. The ablation device of claim 1, wherein the dielectric layer extends distally beyond the distal-most end of the electrically-conductive layer to direct current into the first balun.

14. A system, comprising:
a generator assembly; and
an ablation device operably associated with the generator assembly, the ablation device including:
a feedline having an inner conductor, an outer conductor coaxially-disposed around the inner conductor, and a dielectric material disposed therebetween, the inner conductor having a first diameter;

an elongated electrically-conductive member disposed at a distal end of the inner conductor and having a second diameter different than the first diameter;

a dielectric layer coaxially disposed around a distal portion of the outer conductor;

a first balun operably associated with a first operating frequency, the first balun including an electrically-conductive layer coaxially disposed around a proximal portion of the dielectric layer, wherein the dielectric layer extends distally beyond a distal-most end of the inner conductor; and a second balun operably associated with a second operating frequency, wherein the second balun is electrically coupled to the outer conductor.

15. The system of claim 14, wherein the ablation device further includes a sheath including a substantially tubular member defining a lumen therein, wherein the lumen is configured to contain at least a portion of the ablation device therein.

16. The system of claim 15, further comprising a coolant supply system in fluid communication with the lumen.

17. The ablation device of claim 14, wherein the dielectric layer extends distally beyond the distal-most end of the electrically-conductive layer to direct current into the first balun.

18. An ablation device, comprising:

a feedline including an inner conductor having a distal end and a first diameter, an outer conductor coaxially disposed around the inner conductor, and a dielectric material disposed therebetween;

an elongated electrically-conductive member longitudinally-disposed at the distal end of the inner conductor and having a proximal end and a second diameter different than the first diameter;

a dielectric layer coaxially disposed around a first portion of the outer conductor;

a first balun disposed over the first portion of the outer conductor and positioned so that a distal end of the first balun is located at a first distance from the proximal end of the elongated electrically-conductive member, the first balun including an electrically-conductive layer coaxially disposed around a proximal portion of the dielectric layer, wherein the dielectric layer extends distally beyond a distal-most end of the inner conductor, and wherein a proximal end of the electrically-conductive layer is adapted to allow for connection to the outer conductor; and a second balun disposed over a second portion of the outer conductor and positioned so that a distal end of the second balun is located at a second distance from the proximal end of the elongated electrically-conductive member.

* * * * *